United States Patent [19]
Brown et al.

[11] Patent Number: 5,621,159
[45] Date of Patent: Apr. 15, 1997

[54] METHOD AND APPARATUS FOR DETERMINING FAN BEARING FRICTION

[75] Inventors: Alan E. Brown, Georgetown; Louis E. Cano, Pflugerville, both of Tex.

[73] Assignee: Dell USA L.P., Austin, Tex.

[21] Appl. No.: 552,179

[22] Filed: Nov. 2, 1995

[51] Int. Cl.$^6$ ................................................... G01N 19/02
[52] U.S. Cl. ................................................................. 73/9
[58] Field of Search ............................ 73/9, 10; 340/682

[56] References Cited

U.S. PATENT DOCUMENTS

| | | | |
|---|---|---|---|
| 2,928,275 | 3/1960 | Wadsworth | 73/9 |
| 3,795,131 | 3/1974 | Wade et al. | 73/9 |
| 4,204,425 | 5/1980 | Mallick, Jr. | 73/116 |

*Primary Examiner*—Robert Raevis
*Attorney, Agent, or Firm*—Stanford & Bennett LLP; Gary R. Stanford

[57] ABSTRACT

A fan test system and method for determining fan bearing friction and available life, including a power controller for changing the fan's power level for at least a predetermined time period and a measuring device for measuring the change in rotation of the fan. A memory is preferably coupled to the power controller for storing a plurality of rotation values for providing a history of fan bearing performance. A current sensor or current limiter is preferably coupled in series with the fan, where the measuring device detects voltage pulses or poles of the fan. The power controller preferably includes a timer for determining the time period and a counter for counting rotation events. The power controller also preferably includes a control circuit for controlling a switch coupled between a power source and the fan. In a first embodiment, the power controller removes power from the fan for a relatively short period of time during normal operation while the fan is operating at a desired operating speed or energy level. In a second embodiment, the power controller activates the fan from a rest position and the measuring device measures the spin-up rotation of the fan. In a third embodiment, the power controller controls a variable power source for incrementally increasing the voltage applied to the fan during startup for determining a startup voltage.

14 Claims, 3 Drawing Sheets

METHOD AND APPARATUS FOR DETERMINING FAN BEARING FRICTION

FIELD OF THE INVENTION

The present invention relates to cooling fans, and more particularly to remotely measuring and monitoring bearing friction of a fan over time to determine fan performance and to predict potential failure.

DESCRIPTION OF THE RELATED ART

Cooling fans are commonly used in electronic devices including personal computers (PCs) for assisting in heat transfer. Such forced air cooling is a standard thermal management tool for desktop and server PCs, where a primary fan cools the entire system during operation. Single purpose fans are also known, such as a dedicated fan for a microprocessor, such as the P6 microprocessor manufactured by the Intel Corporation.

Generally, a fan operates to exchange heated air within a system with cooler external air. Failure of a primary or single purpose fan is undesirable since such failure usually requires that the electronic system be shut down to replace or otherwise service the fan. If the fan failure is undetected, thermal buildup results causing critical components to operate in thermally stressed conditions, thereby limiting the life of those components. Even worse, undetected fan failure could lead to catastrophic failure and lead to damage of one or more components in the system.

The most common type of fan used in PCs are brushless DC fans. The most common cause of failure of DC brushless fans is aging bearings, where the fan's rotating bearings wear out due to frictional build-up. To date, there is no known means or method for remotely monitoring fan bearing wear-out during operation or even while an electronic device, such as a computer system, is in service. Remote monitoring refers to measuring the bearing friction automatically without human intervention, preferably during operation. Mechanical measurement of torque is known for testing fans, but such testing is typically performed during or immediately after manufacture and before installation of the fan within a system. Once installed, the condition of the fan has simply not been monitored. This is true even though some fans include an internal tachometer for measuring the fan's RPM. However, the tachometer is often used for fan speed control rather than for measuring bearing friction.

Fan manufacturers commonly specify an end of life parameter, which is usually a percentage decrease of revolutions per minute (RPM) from an initial RPM value when the fan is new. However, this specification is invariably extreme, such as a thirty percent reduction of RPM from the initial RPM value. This particularly extreme specification is indicative of a runaway condition where the fan has already failed or is on the verge of failure. Thus, the first indication of any problem with the fan is usually when it fails, resulting in down time or possible catastrophic malfunction.

It is desired to periodically monitor the status of a fan during operation. Such information is useful for determining when the fan is operating in a marginal manner and requires replacement.

SUMMARY OF THE INVENTION

A fan test system and method for determining bearing friction of a fan according to the present invention includes a power controller for changing the power level provided to the fan for at least a predetermined time period and a measuring device for measuring the rotation of the fan during the predetermined time period. The measuring device measures the change of rotation of the fan during the time period for determining a rotation timing value indicative of the bearing friction of the fan. In particular, the rate of change of the rotation of the fan is directly indicative of the fan bearing friction, which, in turn, is indicative of the relative life of the fan. In the preferred embodiment, a memory is coupled to the power controller, where the power controller periodically tests the fan and stores the corresponding rotation timing values in the memory. The periodic rotation values provide a history of fan bearing performance, which is used for determining the status and for predicting the remaining life of the fan.

The measuring device may be a tachometer externally coupled to the fan or incorporated within the fan itself. In the preferred embodiment, a current sensor or current limiter is coupled in series with the fan, where the measuring device comprises a rotation detection device which detects the voltage or current pulses resulting from the motor's armature rotating past magnetic poles of the motor magnet(s). A twelve-volt DC fan typically has four magnetic poles situated every 90° of rotation of the blades and armature. The rotation of the fan is preferably determined by counting rotation events, such as the number of voltage pulses indicative of the "poles" of the fan. The power controller preferably includes a timer for determining the time period and a counter for counting rotation events.

The power controller also preferably includes a control circuit for controlling a switch, such as a relay, transistor, MOSFET, etc., where the switch is coupled between a power source and the fan. The power controller changes the power level provided to the fan by either connecting the power source to, or disconnecting the power source from, the fan. The control circuit and the measuring device may be incorporated within a single microcontroller for controlling the switch and monitoring the fan.

In a first embodiment according to the present invention, the power controller removes power from the fan for a relatively short period of time, such as about a second, during normal operation where the fan is operating at any desired speed or energy level. A distinct advantage of this method is that the fan is interrupted for a very short-time, so that cooling operation is substantially unaffected. The rotation timing value indicates a spin-down rate of the fan indicative of the fan bearing friction. Since the power source is effectively removed from the fan, the ratio of the kinetic energy stored in the fan's rotor mass versus the bearing friction defines the spin-down rate of the rotor. Since the rotor mass is constant, the spin-down rate indicates the fan's bearing friction. The slower the spin-down rate, the less the fan bearing friction and hence the greater the "health" of the fan. The power controller tests the fan in this manner periodically and stores a plurality of rotation timing values in a memory for providing a history of bearing performance for the fan.

In the first embodiment, a current limiter, such as a relatively high value resistor, is coupled between the fan and power source when the switch is opened, thereby effectively shunting current from the fan. However, the current limiter enables the power source to provide a voltage source for sensing the poles of the fan while it is spinning down. Thus, a separate tachometer is not required, thereby simplifying the apparatus. The counter develops a rotation timing value indicative of the spin-down rate or change of RPM during the predetermined period. The rotation timing value is then stored in a history file in the memory.

In a second embodiment according to the present invention, the power controller activates the fan from a rest position and the measuring device measures the spin-up rotation of the fan for a predetermined time from startup. The greater the bearing friction, the smaller the rotation timing value during the predetermined time period. Again, a standard tachometer may be used as the measuring device. In the preferred embodiment, a current sensor, such as a relatively small-valued resistor, is placed in series with the fan and ground. Thus, the measuring device simply detects the voltage pulses across the sense resistor after power is applied for indirectly measuring the poles of the fan during spin-up. This spin-up test is preferably performed periodically for developing a plurality of spin-up or rotation timing values, which are stored in a memory for providing a history of bearing performance for the fan.

In a third embodiment according to the present invention, the power controller controls a variable power source for incrementally increasing the voltage applied to the fan during startup. A fan typically has a specified minimum startup voltage, which increases with additional bearing friction over time. In this manner, the value of the startup voltage is indicative of the fan bearing friction. The voltage of the variable power source is increased by an incremental amount until the fan begins rotating as determined by the measuring device, which detects rotation of the fan. Once the fan begins rotating, a startup voltage value indicative of fan bearing friction is determined. A plurality of startup voltage values may then be determined and stored in a memory for developing a history of bearing performance over time.

In this manner, it is appreciated that a method and system for determining fan bearing friction according to the present invention provides a way of monitoring the status of the fan by indirectly measuring the fan bearing friction after a change in the fan's power level. Rotation timing or startup voltage values are preferably collected periodically over time and stored in a memory. The history of bearing performance may then be graphed or otherwise compared for determining the status or the mean time to failure (MTTF) of the fan.

BRIEF DESCRIPTION OF THE DRAWINGS

A better understanding of the present invention can be obtained when the following detailed description of the preferred embodiment is considered in conjunction with the following drawings, in which.

DETAILED DESCRIPTION OF THE PREFERRED EMBODIMENT

Figure 1:
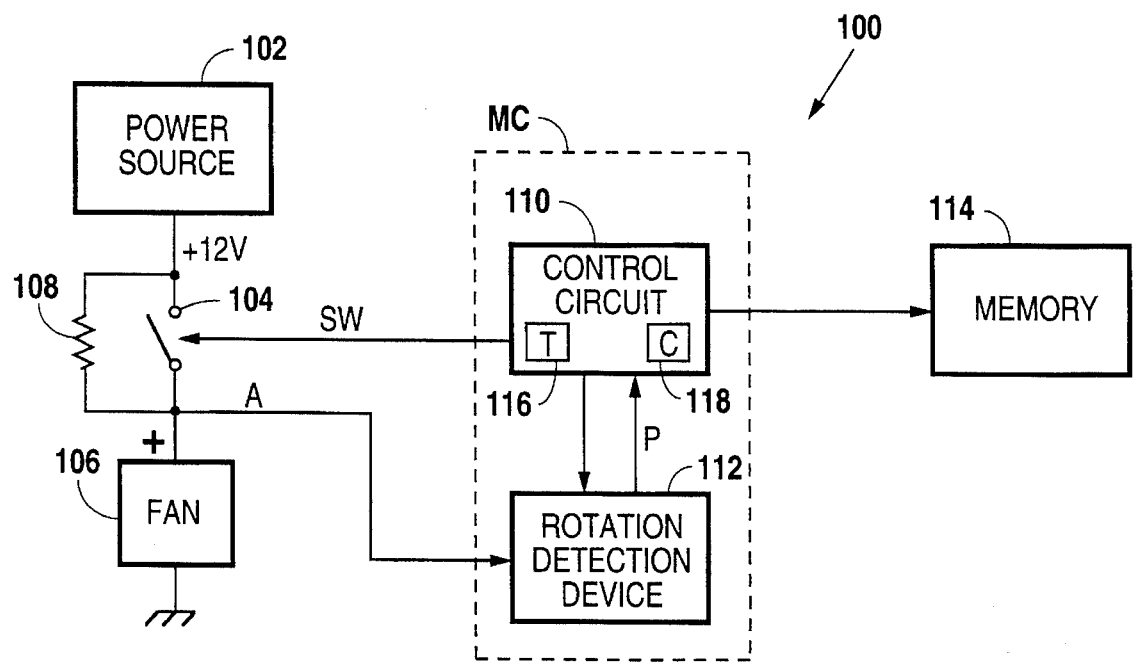
FIG. 1 is a block diagram illustrating a fan test system according to one embodiment of the present invention.

FIG. 1 is a simplified block diagram illustrating a fan test system 100 according to one embodiment of the present invention. A twelve volt power source 102 provides a twelve volt power signal, referred to as +12 V, for providing power to a fan 106. The fan 106 is preferably a 12 volt, DC brushless type fan including a multiple pole motor for cooling an electronic device, such as a personal computer (PC) (not shown). Although a DC fan is shown, it is understood that the present invention applies to any type of fan that operates with any corresponding alternating or direct current source as desired. The +12 V signal is applied to one terminal of a controllable, single pole-single throw (SPST) switch 104, having its other terminal connected to the positive terminal of the fan 106. The negative terminal of the fan 106 is connected to ground. A current limit resistor 108 is preferably coupled across the terminals of the switch 104 between the +12 V signal and the positive terminal of the fan 106.

A control circuit 110 asserts a switch control signal SW for turning on and off or otherwise for opening and closing the switch 104. The switch 104 may preferably be implemented in any one of several ways, such as a relay, a metal-oxide semiconductor field-effect transistor (MOSFET), a bipolar transistor, etc. The control circuit 110 asserts the SW signal for closing the switch 104 to connect the +12 V signal to the fan 106 to activate the fan 106. The control circuit 110 is coupled to a measuring or rotation detection device 112, which monitors the voltage of the positive terminal of the fan 106, otherwise referred to as signal A. The control circuit 110 is also coupled to provide data to a memory device 114 for storing data values, as described further below.

Operation of the fan test system 100 is now described. The control circuit 110 preliminarily asserts the SW signal to activate the switch 104 for powering the fan 106 during normal operation. While the fan 106 is operating at full speed or at any desired operation speed or energy level, the control circuit 110 opens the switch 104 for a predetermined time period. During the predetermined time period, the power source 102 is connected to the fan 106 through the resistor 108, which is preferably a relatively high value resistor, such as approximately 15 KΩ. Since the value of the resistor 108 is relatively high, the current supplied to the fan 106 is insufficient to enable operation, so that the fan 106 is effectively turned off during the predetermined time period. The fan 106 begins to slow down so that its revolutions per minute (RPM) decreases during the predetermined time period.

Figure 2:
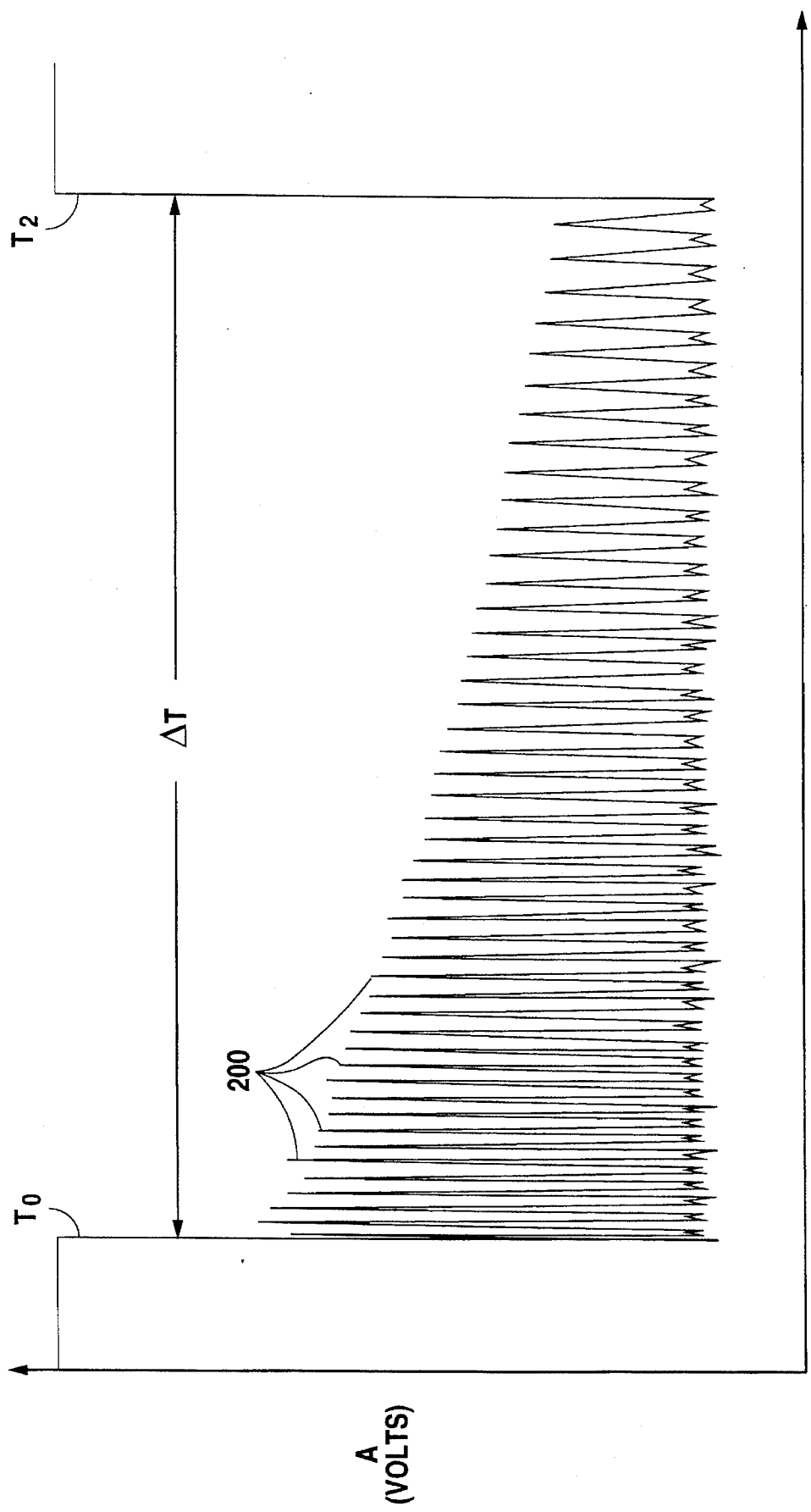
FIG. 2 is a graph of the A signal of FIG. 1 versus time during a test period.

During the time period, the armature of the fan 106 passes its magnetic poles, thereby creating voltage pulses on the A signal as detected by the rotation detection device 112. FIG. 2, further described below, illustrates the voltage pulses appearing on the A signal indicative of the poles of the fan 106 while it is spinning down. The rotation detection device 112 detects the voltage pulses during the predetermined time period and preferably provides a signal P indicative of each pole to the control circuit 110. The control circuit 110 preferably includes a counter 118, which counts the number of pulses detected by the rotation detection device 112 during the predetermined time period. Upon completion of the predetermined time period, the control circuit 110 asserts the SW signal to close the switch 104 to continue normal operation of the fan 106. The control circuit 110 preferably provides the pole count or rotation timing value to the memory device 114 for storage.

The control circuit 110 preferably includes a timer 116 or the like for timing the predetermined time period. The predetermined time period is preferably a very short time in a period, such as from a half second to one second, so that the normal cooling operation of the fan 106 is substantially unaffected, yet long enough to enable a relatively accurate measure of spin-down rate. The control circuit 110 then reasserts the SW signal to continue normal operation of the fan 106.

The rotation detection device 112 may be implemented in any one of several ways. For example, it could be implemented as a standard tachometer for measuring the RPM of the fan 106 using any one of several known methods. Many fans are manufactured with built-in tachometers which may be used instead of the rotation detection device 112. However, this would require a more expensive fan. In the preferred embodiment, the rotation detection device 112 monitors the voltage of the A signal through the resistor 108, where voltage is developed from the power source 102. The rotation detection device 112 could monitor any rotation events such as the voltage rising above a predetermined threshold, such as approximately 7 volts, or it could monitor the peak values of the voltage pulses of the A signal during the predetermined time period. The rotation detection device 112 could then assert a digital pulse signal on the P signal identifying each pole or voltage pulse on the A signal to be counted by the control circuit 110.

The control circuit 110 and the rotation detection device 112 could be implemented in any one of several ways, such as a single microcontroller MC as indicated by the dashed lines in FIG. 1. A microcontroller includes at least one digital output port for asserting the SW signal and analog voltage inputs for measuring the A signal. Furthermore, typical microcontrollers include timers and counters for timing the predetermined time period and counting pulses for determining the rotation timing value. The rotation timing value is then asserted through an output port to the memory device 114 for storage.

The pole count or rotation timing value determined during spin-down after power is removed is indicative of the fan bearing friction of the fan 106. The ratio of the kinetic energy stored in the rotor mass versus the bearing friction of the fan defines the spin-down rate of the rotor. Since the rotor mass is constant, the rotation timing value measured during spin-down is indicative of the bearing friction of the fan 106. In particular, the greater the number of poles during spin-down of the fan 106, the less the fan bearing friction, and therefore the "healthier" the fan 106.

Over time, as the fan bearing friction increases, the number of poles measured during each test period decreases. In the preferred embodiment, the control circuit 110 is programmed to periodically test the fan 106 by measuring another spin-down or rotation timing value and store the value into the memory device 114. The resulting file in the memory device 114 provides a history of the bearing performance of the fan 106 over time. This history file is then retrieved and displayed on a graph or otherwise analyzed for monitoring and determining the status of the fan 106. Such status can be monitored on a periodic basis, such as weekly, monthly, yearly, etc.

FIG. 2 is a graph of the voltage of the A signal versus time for the predetermined time period during operation. At a time T0, the control circuit 110 deasserts the SW signal for opening the switch 104 and a series of voltage pulses 200 appear on the A signal. As described previously, the control circuit 110 keeps the switch 104 open for the predetermined time period, shown as ΔT, until a time T2, at which time the control circuit 110 reasserts the SW signal for closing the switch 104. As described previously, the rotation detection device 112 is implemented in any manner to detect the voltage pulses 200 provided during the predetermined time period ΔT.

Figure 3:
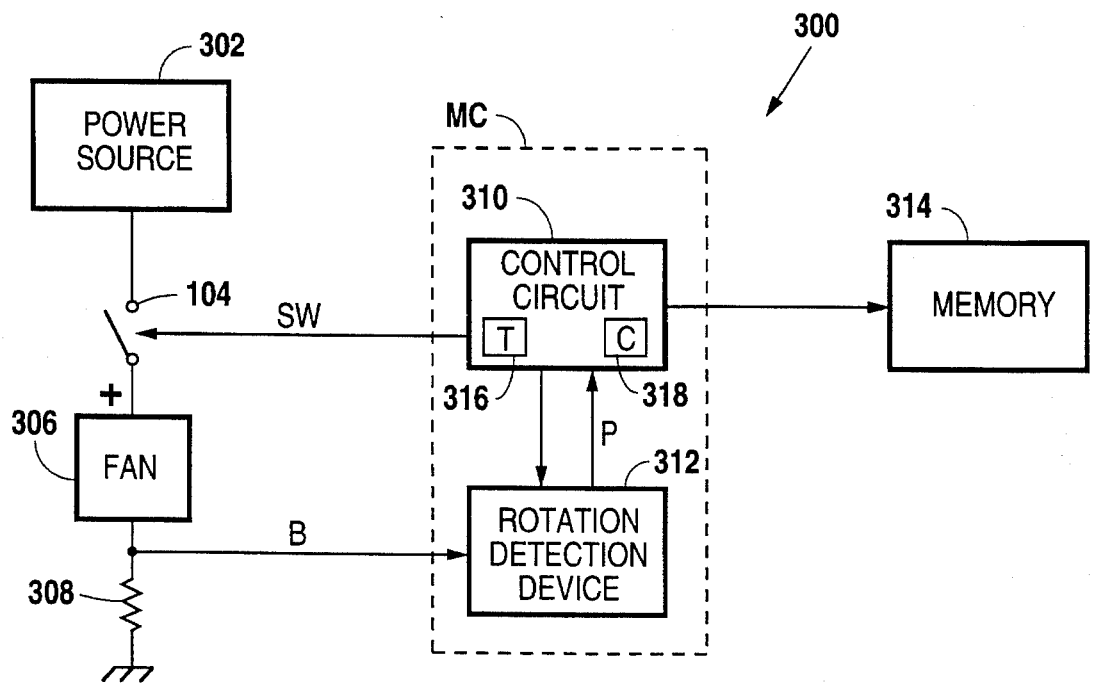
FIG. 3 is a block diagram of a fan test system implemented according to an alternative embodiment of the present invention.

Referring now to FIG. 3, a fan test system 300 is shown implemented according to an alternative embodiment of the present invention. Again, a power source 302 provides the +12 V signal, where the power source 302 is similar to the power source 102. The +12 V signal is provided to one terminal of a controllable SPST switch 304, having its other terminal connected to the positive terminal of a fan 306. The switch 304 and the fan 306 are preferably similar to the switch 104 and fan 106. In this embodiment, however, the negative terminal of the fan 306 is provided to one end of a sense resistor 308, having its other end connected to ground. Of course, any type of current sensor could be used rather than the sense resistor 308. It is noted that since the sense resistor 308 is always in series with the fan 306 during normal operation and during testing, it is preferably a relatively small resistor, such as approximately 2.2Ω.

A control circuit 310 is provided for asserting an SW signal to the switch 304 in a similar manner as described for the switch 104. A rotation detection device 312 monitors the voltage of the junction between the resistor 308 and the fan 306, where this junction is referred to as a signal B. Alternatively, the rotation measuring device can be implemented by any standard internal or external tachometer. The control circuit 310 is further coupled to a memory device 314 for storing values indicative of the fan bearing friction of the fan 306.

Operation of the fan test system 300 is as follows. The control circuit 310 initially deasserts the SW signal to completely turn off the fan 306. The fan 306 is thus initially at rest to begin the test. The control circuit 310 then asserts the SW signal to close the switch 304 and to turn on the fan 306. The rotation detection device 312 correspondingly monitors the voltage of the B signal to detect voltage pulses during spin-up of the fan 306. The rotation detection device 312 operates in a similar manner as the rotation detection device 112 for monitoring the voltage pulses across the sense resistor 308. During a predetermined time period from startup of the fan 306, preferably determined by a timer 316 within the control circuit 310, the control circuit 310 counts the voltage pulses measured by the rotation detection device 312. A counter 318 is preferably provided for this purpose, which is similar to the counter 118 of the control circuit 110. After the predetermined time period is completed, a spin-up pole count or rotation timing value is determined by the control circuit 310, which value may be stored in the memory device 314.

The fan test system 300 is similar to the fan test system 100, except that the fan 306 is initially turned off and at rest before the test is initiated. The method of testing by the fan test system 300 is not as convenient as the method used by the fan test system 100, since the fan 306 must be completely turned off for testing. The control circuit 310 periodically turns off the fan 306 until the fan blades are completely at rest and then turns on the fan 306 by closing the switch 304. The control circuit 310 then counts the number of voltage pulses that occur during the predetermined period of time. Once again, the predetermined time period is preferably very short, such as between half a second and one second, where the rotation timing value indicates the bearing friction of the fan 306. The time period is sufficient for accurate determination of spin-up rotation. The greater the bearing friction of the fan 306, the less the rotation timing value measured.

The spin-up test is performed on a periodic basis and the resulting rotation timing values are stored in the memory 314 for developing a history of bearing performance of the fan 306. Thus, a history file stored in the memory 314 may be retrieved on a periodic basis for determining the status of the fan 306. In this manner, a determination of the status of the fan 306 is achieved, which may be used as an indication of when the fan 306 should be replaced. Also, the control circuit 310 and the rotation detection device 312 may be implemented in any one of several manners, such as by a single microcontroller MC in a similar manner as described for the fan test system 100 of FIG. 1.

Figure 4:
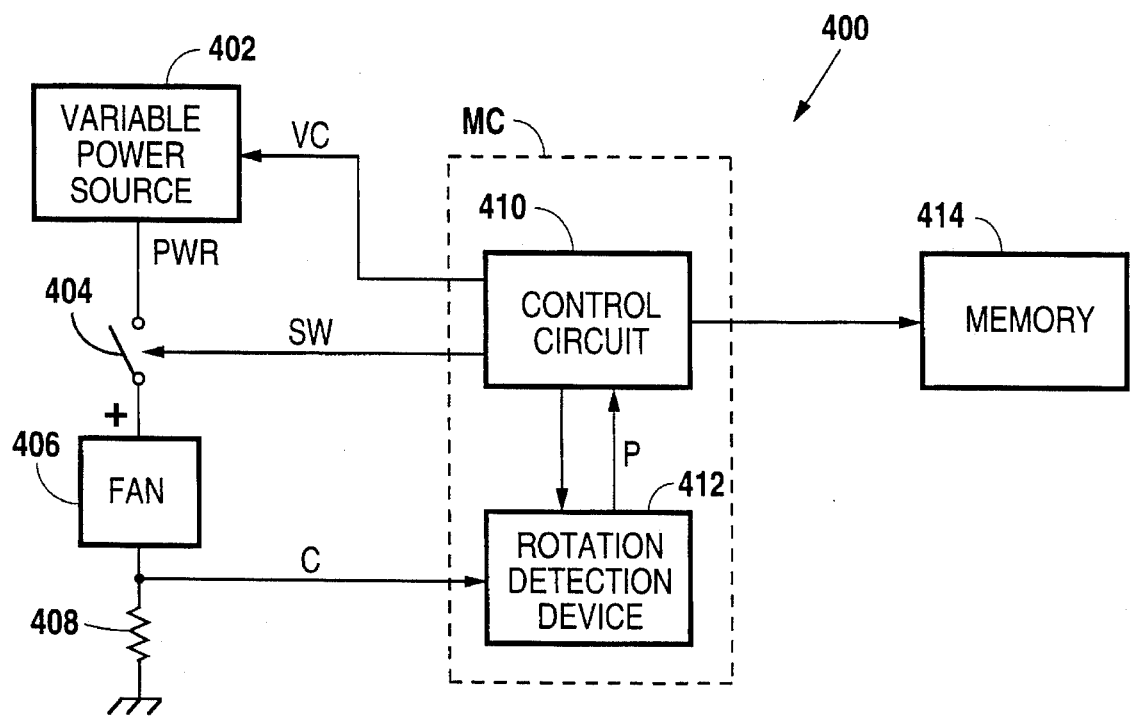
FIG. 4 is a block diagram of another fan test system according to another alternative embodiment of the present invention.

Referring now to FIG. 4, another fan test system 400 is shown according to an alternative embodiment of the present invention. This embodiment recognizes that the minimum startup voltage of a fan increases over time due to increased bearing friction. In one particular test performed, a Panaflo model no. PBM-OBA12M brushless DC fan was operated for 1,581 hours at 50° C. The fan's minimum startup voltage increased from 3.118 V to 3.962 V as a result of operating the fan, which is an increase of 27.07%. Thus, changes in startup voltage are indicative of increased bearing friction due to aging of a fan.

A variable power source 402 provides a power signal PWR to one terminal of a controlled SPST switch 404, having its other terminal connected to the positive terminal of a fan 406. The negative terminal of the fan 406 is connected to one end of a sense resistor 408, having its other end connected to ground. The switch 404 and the fan 406 are preferably similar to the switches 104, 304 and the fans 106, 306, respectively. However, the variable power source 402 asserts the PWR signal at incremental values between zero and twelve volts. The incremental value is preferably 100 millivolts (mV) or any other convenient incremental value for determining the startup voltage of the fan 406.

A control circuit 410 asserts a VC signal to the variable power source 402, where the VC signal indicates the amount of voltage to be applied on the PWR signal by the variable power source 402. For example, the VC signal could be a digital value having a binary value indicative of the number of 100 mV increments to provide on the PWR signal. The control circuit 410 also asserts the SW signal for controlling the switch 404. The control circuit 410 is coupled to a rotation detection device 412 implemented in a similar manner as the rotation detection devices 112, 312. The rotation detection device 412 monitors the negative terminal of the fan 406 through a signal C in a similar manner as described for the fan test system 300. However, the rotation detection device 412 need not measure the rate or change of rotation, but need only determine whether or not the fan 406 is rotating. The control circuit 410 is coupled to a memory device 414, which is similar to the memory devices 114, 314.

Figure 5:
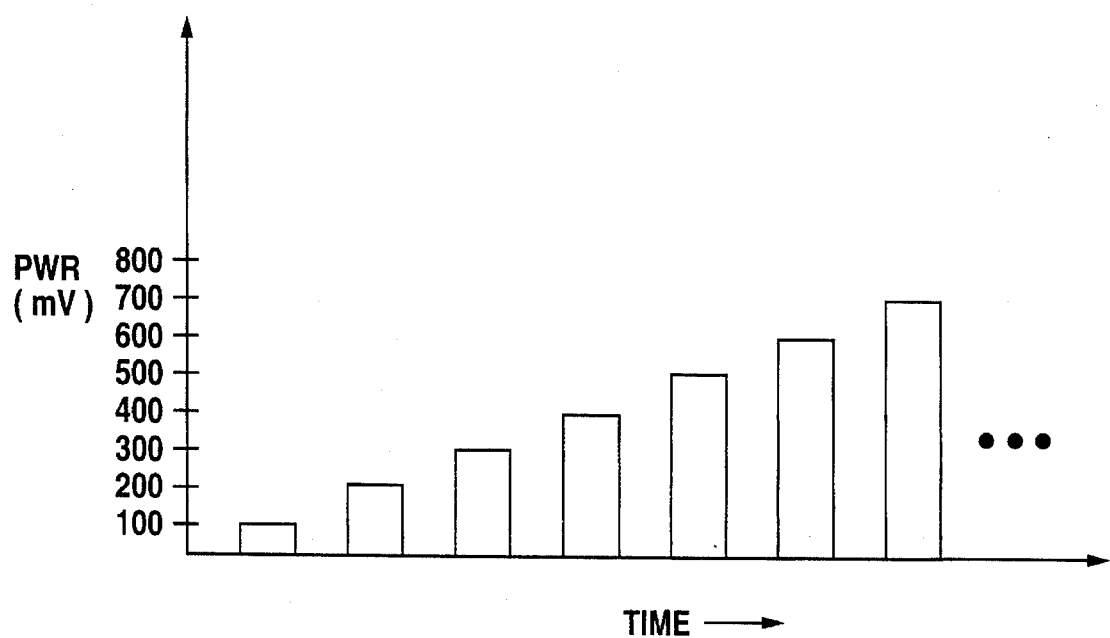
FIG. 5 is a graph of the V signal versus time of FIG. 4 during startup test.

Operation of the fan test system 400 is as follows. As described above for the fan test system 300, the control circuit 410 initially opens the switch 404 to completely turn off the fan 406. The control circuit 410 then controls the variable power source 402 to apply an incremental voltage on the PWR signal until the PWR signal stabilizes. Then the control circuit 410 closes the switch 404 and the rotation detection device 412 monitors the C signal to determine if the fan 406 is rotating. If no voltage pulses are detected by the rotation detection device 412 on the C signal as determined by the control circuit 410, then the control circuit 410 opens the switch 404 and controls the variable power source 402 to increment the voltage on the PWR signal by another incremental amount. In the preferred embodiment, each incremental amount is 100 mV, so that the PWR signal is incrementally increased during each iteration to assert 100 mV, 200 mV, 300 mV, etc. FIG. 5 is a graph of the voltage of the C signal versus time illustrating the incremental voltage values applied to the fan 406.

Eventually, the voltage of the PWR signal is increased to a sufficient voltage to start the fan 406. Once the startup voltage is reached, the control circuit 410 has determined a startup voltage value, which may either represent the voltage level of the PWR signal, or otherwise the number of incremental voltage values representing the startup voltage. For example, if the fan 406 begins to operate at 5 V, then the number of 100 mV increments is 50. The control circuit 410 preferably stores the startup voltage value in the memory 414.

In the preferred embodiment, the control circuit 410 periodically performs the startup voltage test and correspondingly stores each startup voltage value in the memory 414. The startup voltage values stored in the memory device 414 provide a history of bearing performance of the fan 406. It is known that over a fan's lifetime, the startup voltage of the fan increases due to additional bearing friction of the fan 406, so that the startup voltage values are indicative of the bearing friction of the fan 406 over time. Again, the history file within the memory 414 may be periodically monitored over time to monitor the status of the fan 406. This information can be used to monitor the status of the fan 406, which helps to determine when to replace the fan 406 before it fails.

As described previously, the control circuit 410 and the rotation detection device 412 can be implemented in any one of several ways as known to those skilled in the art, and may preferably be implemented using a microcontroller MC in a similar manner as described previously.

Although a method and apparatus for determining fan bearing friction according to the present invention has been described in connection with several alternative embodiments, these embodiments are not intended to be limited to the specific form set forth herein, but on the contrary, they are intended to cover such alternatives, modifications, and equivalents, as can be reasonably included within the spirit and scope of the invention as defined by the appended claims.

We claim:

1. A fan test system for measuring the bearing friction of a fan receiving power from a power source during normal operation, comprising:

a switch for coupling between the fan and the power source;

a current limiter coupled in parallel with said switch;

a power controller coupled to said switch to test the fan by controlling said switch to interrupt power to the fan for at least a predetermined time period; and a measuring device coupled to said current limiter for detecting voltage pulses of the fan to determine a spin-down rate value during said predetermined time period indicative of the bearing friction of the fan.

2. The fan test system of claim 1, wherein said predetermined time period is approximately one second.

3. The fan test system of claim 1, wherein said current limiter comprises a resistor having a resistance sufficient to essentially remove operating current from the fan.

4. The fan test system of claim 1, wherein said power controller further includes:

a timer for indicating said predetermined time period; and a counter coupled to said measuring device for counting said voltage pulses.

5. The fan test system of claim 1, further comprising:

memory coupled to said power controller; and said power controller being programmed to periodically test the fan for generating a plurality of spin-down rate values, and for storing each of said plurality of spin-down rate values in said memory for providing a history of bearing performance.

6. The fan test system of claim 1, wherein said measuring device comprises a tachometer.

7. The fan test system of claim 1, wherein said control circuit and said measuring device comprise a microcontroller.

8. A method for determining the bearing friction of a fan during normal operation and for monitoring the fan over time, comprising the steps of:

during operation, periodically disconnecting power from the fan for a predetermined time period;

measuring a spin-down rate value for the fan during each predetermined time period to generate a plurality of spin-down rate values over time; and storing each of the plurality of spin-down rate values in a memory for establishing a history of bearing performance of the fan.

9. The method of claim 8, further comprising the step of:

after each occurrence of said step of periodically disconnecting power from the fan for a predetermined time period, reconnecting power to the fan to maintain substantially unaffected operation of the fan.

10. A computer system, comprising:

a fan for cooling the computer system during normal operation;

a power source for providing operating power to said fan;

a switch coupled to said fan for controlling power to said fan;

a control circuit coupled to said switch for temporarily interrupting power to said fan for a predetermined period of time during normal operation of the computer system without substantially affecting the cooling function of said fan; and a fan speed measuring device coupled to said fan for measuring a rate value during said predetermined time period indicative of the spin-down rate of said fan.

11. The computer system of claim 10, wherein said predetermined time period is approximately one second.

12. The computer system of claim 10, further comprising:

a current limiter coupled in parallel with said switch for enabling current flow through said fan while operating power is interrupted; and said fan speed measuring device being coupled to said current limiter and operable to detect voltage pulses of said fan.

13. The computer system of claim 12, wherein said current limiter comprises a resistor having a resistance sufficient to decrease the current through said fan below a minimum operating current level.

14. The computer system of claim 10, further comprising:

a memory coupled to said fan speed measuring device and said control circuit; and said control circuit periodically interrupting power to said fan for generating a plurality of rate values, and storing each of said plurality of rate values in said memory for providing a history of bearing performance.

* * * * *